US012383720B2

United States Patent
Kumar et al.

(10) Patent No.: US 12,383,720 B2
(45) Date of Patent: Aug. 12, 2025

(54) UNIVERSAL DISINFECTING CAP WITH EXPANDABLE SLITTED OPENING

(71) Applicant: Becton, Dickinson and Company, Franklin Lakes, NJ (US)

(72) Inventors: Manish Kumar, Arrah (IN); Praveen Nalawade, Karnataka (IN); Shashwat Jain, Indore (IN); Kadamb Gupta, Uttar Pradesh (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 790 days.

(21) Appl. No.: 17/722,053

(22) Filed: Apr. 15, 2022

(65) Prior Publication Data

US 2023/0330407 A1    Oct. 19, 2023

(51) Int. Cl.
```
A61M 39/16    (2006.01)
A61L 2/18     (2006.01)
A61L 2/26     (2006.01)
A61M 39/20    (2006.01)
A61L 101/34   (2006.01)
```
(52) U.S. Cl.
CPC ............. *A61M 39/162* (2013.01); *A61L 2/18* (2013.01); *A61L 2/26* (2013.01); *A61M 39/20* (2013.01); *A61L 2101/34* (2020.08); *A61L 2202/24* (2013.01)

(58) Field of Classification Search
CPC ................ A61L 29/00; A61L 2202/24; A61M 2205/0205; A61M 39/162; A61M 39/20
See application file for complete search history.

(56) References Cited

U.S. PATENT DOCUMENTS

| 8,197,749 B2 | 6/2012 | Howlett et al. |
| 10,871,246 B2 | 12/2020 | Marici et al. |
| 2019/0234540 A1 | 8/2019 | Marici et al. |

FOREIGN PATENT DOCUMENTS

| WO | 2019199750 A1 | 10/2019 |
| WO | 2020160064 A1 | 8/2020 |

OTHER PUBLICATIONS

"PCT International Search Report and Written Opinion in PCT/US2023/018488 dated Aug. 7, 2023, 13 pages".

*Primary Examiner* — Deanna K Hall
(74) *Attorney, Agent, or Firm* — SERVILLA WHITNEY LLC (57) ABSTRACT

A cap is described for connection to a needleless connector having an open lumen, the cap includes a housing having a top wall and sidewall forming a first cavity, a flexible container, an porous absorbent material and a sealing rubber. The flexible container includes an inner thread on an inner surface, the inner thread being sufficient to interlock with a mating feature of a female needleless connector. The inner surface of the flexible container defines a second cavity. The sidewall of the housing having a split-thread protrusion integrally formed with the distal wall, an outer thread disposed on an outer surface of the split-thread protrusion, the outer thread being sufficient to interlock with a mating feature of a male needleless connector. The second cavity configured to define a chamber to contain an absorbent reservoir material, a sealing rubber and disinfectant or antimicrobial agent.

22 Claims, 7 Drawing Sheets

UNIVERSAL DISINFECTING CAP WITH EXPANDABLE SLITTED OPENING

TECHNICAL FIELD

The present disclosure generally relates to a device for disinfecting and sterilizing multiple types of connectors including both male luer connectors and female luer connectors. Generally, exemplary embodiments of the present disclosure relate to the fields of medical caps and medical disinfection caps, and in particular caps and/or disinfection caps for uses with fluid luer connectors.

BACKGROUND

Vascular access devices (VAD's) are commonly used therapeutic devices and include intravenous (IV) catheters. There are two general classifications of VAD's, peripheral catheters and central venous catheters. Bacteria and other microorganisms may gain entry into a patient's vascular system from access hubs, ports and valves upon connection to the VAD to deliver the fluid or pharmaceutical. Each access hub, port, valve or connection is associated with some risk of transmitting a catheter related bloodstream infection (CRBSI), which can be costly and potentially lethal.

In order to decrease catheter-related bloodstream infection (CRBSI) cases and to ensure VAD's are used and maintained correctly, standards of practice have been developed, which include disinfecting and cleaning procedures. Disinfection caps have been added to the Society for Healthcare Epidemiology of America (SHEA) guidelines and caps are also incorporated into the Infusion Nurses Standards (INS) guidelines.

In developed markets, when utilizing an IV catheter, a needleless connector will typically be used to close off the system and then subsequently accessed to administer medication or other necessary fluids via the catheter to the patient. INS Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface and possibly lead to a variety of catheter related complications including the CRBSI. Nurses will typically utilize a 70% isopropyl alcohol (IPA) pad to complete this disinfection task by doing what is known as "scrubbing the hub." However, compliance to this practice is typically very low. In addition to a lack of compliance to "scrubbing the hub", it has also been noted through clinician interviews that there is often a variation in scrub time, dry time and the number of times the needleless connector is scrubbed.

Throughout the sequence of procedures associated with the transmission of a microorganism that can cause a CRBSI, there are many risks of contact or contamination. Contamination can occur during drug mixing, attachment of a cannula, and insertion into the access hub. Because the procedure to connect to a VAD is so common and simple, the risk associated with entry into a patient's vascular system has often been overlooked. Presently, the risk to hospitals and patients is a substantial function of the diligence of the clinician performing the connection, and this diligence is largely uncontrollable.

Currently, caps for male needleless connectors, female needleless connectors, intravenous (IV), and hemodialysis lines use different designs and are therefore limited to the types of connectors to which the cap can be attached. Currently, there are female disinfecting cap devices for disinfecting ISO594-2 type of female threaded fluid luer connectors and there are male disinfecting cap devices for disinfecting ISO594-2 type of male threaded fluid luer connectors. However, there is not a singular universal disinfecting cap device with features allowing it to interface with both a male and female type of threaded connectors. Prior disinfecting caps were designed to fit one type of connector only, and were specific to one particular size and/or shape of connector. Thus, there is a need for a disinfecting device capable of accommodating multiple types of connectors to streamline the disinfecting process.

SUMMARY

One aspect of the present disclosure pertains to a cap having a housing including a top wall, an essentially cylindrical sidewall forming a first cavity, the sidewall having a split-thread integrally formed with the distal wall and an open bottom formed by the cylindrical sidewall with an opening to the first cavity within the housing for receiving a flexible container; the split-thread protrusion of the sidewall having an inner surface and an outer surface and an flexible container disposed within the first cavity, the flexible container having closed distal end comprising a distal wall, an open proximal end, a sidewall extending proximally from the distal wall toward the open proximal end,, the inner surface of the flexible container defining a second cavity to receive a needleless connector having an closed lumen, an inner thread on the inner surface of the flexible container, the inner thread being sufficient to interlock with a mating feature of the female needleless connector, an outer thread on the outer surface of the split-thread protrusion, the outer thread being sufficient to interlock with a mating feature of the male needleless connector; a sealing rubber/foam; absorbent material configured within the second cavity; a disinfectant or an antimicrobial agent; and a cover for maintaining sterility and forming a seal at the open proximal end of the housing and flexible container for maintaining the disinfectant or an antimicrobial agent within the second cavity prior to use of the cap.

In one or more embodiments, the housing extends essentially from an inner surface of the top wall toward the open bottom of the housing. In one or more embodiments, the exterior wall surface of the sidewall of the housing includes an outer thread. In one or more embodiments, the outer thread has an inclined thread pattern. In one or more embodiments, the outer thread has a helical-shaped thread pattern. In one or more embodiments, the exterior wall surface of the sidewall of the housing includes a plurality of grip members. In one or more embodiments, the housing is made of a high density polyethylene or polypropylene material.

In one or more embodiments, the flexible container extends essentially from an inner surface of the top wall toward the open bottom of the housing. In one or more embodiments, the flexible container extends essentially parallel to the sidewall of the housing. In one or more embodiments, the inner thread has an inclined thread pattern. In one or more embodiments, the inner thread have a helical-shaped thread pattern.

The flexible container is disposed in the housing and positioned within the first cavity. The flexible container has an inner surface and an outer surface, the inner surface of the flexible container defining a second cavity. The flexible container has an inner thread on the inner surface of the flexible container.

The cap also includes a porous absorbent material held by the inner wall below the thread or lug using radial compression. The cap also includes a sealing rubber disposed onto the absorbent reservoir material. In one or more embodiments, the porous absorbent material includes a centrally disposed through hole extending from a distal end to a proximal end of the absorbent reservoir material. In one or more embodiments, the sealing rubber is disposed within the centrally disposed through hole of the absorbent reservoir material. In one or more embodiments, the sealing rubber is stacked on top of the absorbent reservoir material using adhesive. In one or more embodiments, the sealing rubber is bonded to the absorbent material with a biocompatible adhesive.

In one or more embodiments, the sealing rubber is in the form of an elongate shaft. In one or more embodiments, the elongate shaft of the sealing rubber is disposed into the though hole of the absorbent reservoir material.

In one or more embodiments, the porous absorbent material surrounds an elongate shaft of the sealing rubber.

In one or more embodiments, the porous absorbent material is a nonwoven material, foam, or a sponge. In one or more embodiments, the porous absorbent material is soaked with a disinfectant or an antimicrobial agent.

In one or more embodiments, the sealing rubber is made of a closed cell foam, a polyethylene foam, a thermoplastic elastomer, a rubber or rubber like foams. In one or more specific embodiments, the sealing rubber is an EPDM sponges, EVA, Buna-N, silicone, vinyl, neoprene, fluoroelastomers, gum rubber.

In one or more embodiments, the cap further includes a disinfectant or the antimicrobial agent.

In one or more embodiments, the disinfectant or the antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

Figure 2:
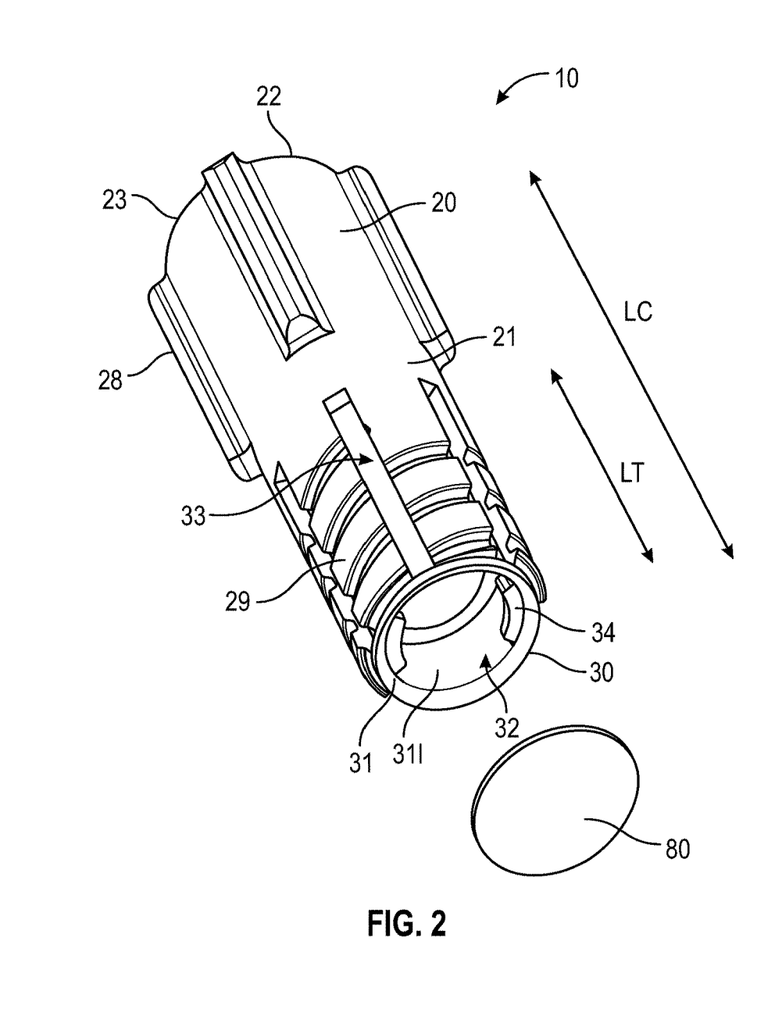
FIG. 2 illustrates a perspective top view of a cap according to an exemplary embodiment of the disclosure.
Figure 3:
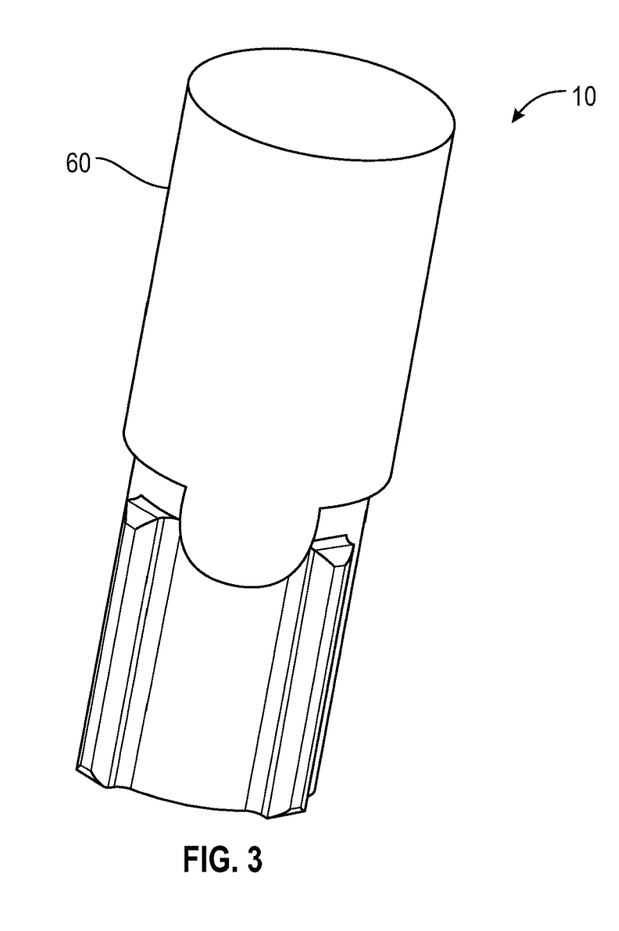
FIG. 3 illustrates a perspective top view of a cover and a cap according to an exemplary embodiment of the disclosure as shown in FIG. 1.

In one or more embodiments, as shown in FIG. 3, the cap includes a cover 60. In one or more embodiments, as shown in FIG. 2, the cap may also include a peel seal 80. In one or more embodiments, the peel seal comprises an aluminum or multi-layer polymer film. In one or more embodiments, the peel seal further comprises a moisture barrier.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

DETAILED DESCRIPTION

Embodiments of the disclosure pertain to a sterile, universal cap for connection to and disinfection of a medical connector having an open or closed lumen, including male connectors and female connectors. The male connectors and female connectors can be male luer connectors and closed female luer connectors used in vascular access procedures. Embodiments of the cap comprise a housing, a flexible container, an absorbent material, a sealing rubber and a cover. Embodiments of the disclosure fit both a male Luer and a closed female Luer connectors with interchangeability. The cap may further comprise a disinfectant or the antimicrobial agent and a cover. The cap provides a mechanical barrier for connectors and contains an antimicrobial agent for disinfection. The cap of the present disclosure also allows the practitioner to streamline the disinfecting process while blocking the lumen of open luer to facilitate the mitigation of the ingress of contaminants and disinfectant into the open lumens of the connectors, thereby reducing risk of the contaminants and disinfectant entering the blood stream.

With respect to terms used in this disclosure, the following definitions are provided.

As used herein, the use of "a," "an," and "the" includes the singular and plural.

As used herein, the term "catheter related bloodstream infection" or "CRBSI" refers to any infection resulting from the presence of a catheter or IV line.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on the vascular access device (VAD). A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe.

As would be readily appreciated by skilled artisans in the relevant art, while descriptive terms such as "lock", "interlock", "hole", "tip", "hub", "thread", "sponge", "prong", "protrusion", "flexible container", "lug", "wall", "top", "side", "bottom" and others are used throughout this specification to facilitate understanding, it is not intended to limit any components that can be used in combinations or individually to implement various aspects of the embodiments of the present disclosure.

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

In an exemplary implementation of the embodiments of present disclosure, a cap, connector cap or disinfecting cap includes integrated thread, or threads, and other features in any and all combinations allowing it to interface with both male and female threaded fittings.

According to further exemplary implementations of the embodiments of the present disclosure, configuration of structural elements making up the flexible container include an inner lug or thread to connect to female medical connectors. Configuration of structural elements making up the housing include one or more split thread protrusions comprising an outer thread to connect to male medical connectors, to facilitate securing of the cap onto a male fitting.

According to still further exemplary implementations of the embodiments of the present disclosure, the split thread sidewall of the housing includes a plurality of cantilevered prongs in which the plurality of cantilevered prongs of the housing may bend in order to allow better interference fit compliance with the fittings.

According to still further exemplary implementations of the embodiments of the present disclosure, female threads are sized and have a thread pattern that will engage with a standard ISO594-2 type of male fitting and/or a male threads that are sized and have a thread pattern that will engage with a standard ISO594-2 type of female fitting.

In one or more embodiments, the female connector may be selected from the group consisting essentially of closed female luer connectors, needle-free connectors, catheter luer connectors, stopcocks, and hemodialysis connectors.

In one or more embodiments, the male connector may be a male luer connector, male lock connector on IV line, intravenous tubing end, a stopcock, male lock luer or any male connectors following ISO-80369-7 dimensions.

Before describing several exemplary embodiments of the disclosure, it is to be understood that the disclosure is not limited to the details of construction or process steps set forth in the following description. The disclosure is capable of other embodiments and of being practiced or being carried out in various ways.

Referring now to the drawings, wherein like reference numerals designate identical or corresponding parts throughout the several views, embodiments of the present disclosure are described as follows.

Figure 1:
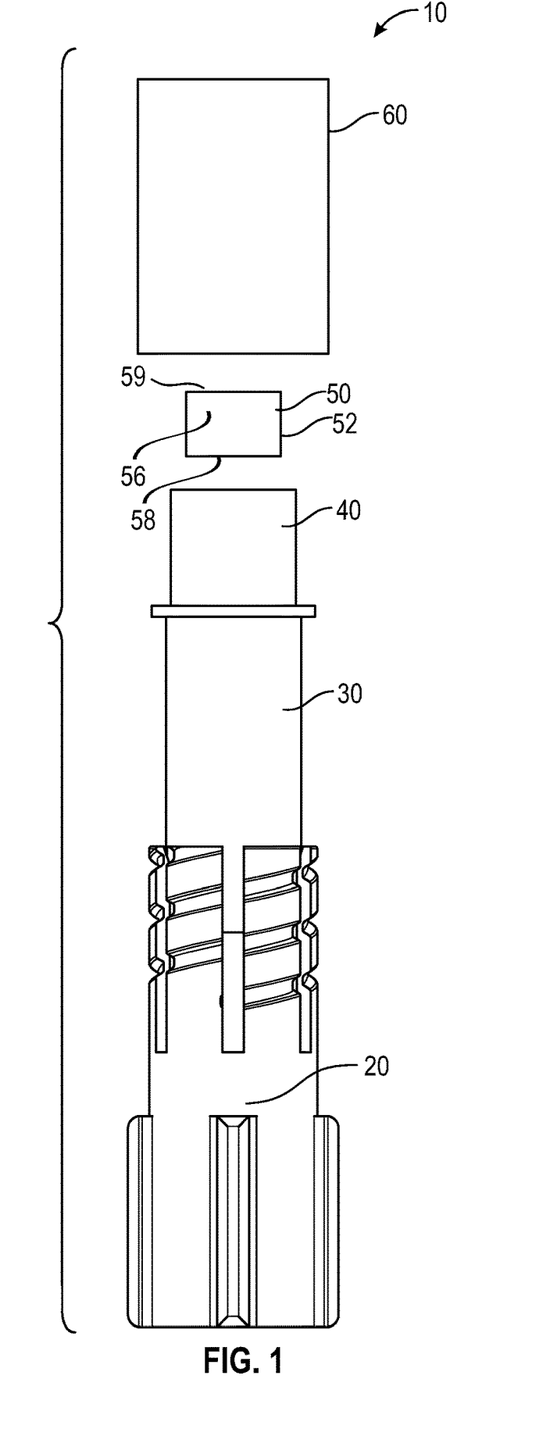
FIG. 1 illustrates an exploded view of an exemplary cap according to an exemplary embodiment of the disclosure.

An exploded view of a cap of the present disclosure, as shown in FIG. 1, relates to a cap 10 including a housing 20, a flexible container 30 disposed within a first cavity of the housing, an absorbent material 40 disposed within a chamber of the flexible container, a sealing rubber 50 and a cover 60. Embodiments of the present disclosure fit both a closed female Luer connectors 90 or male Luer connector 92 with interchangeability.

Figure 4:
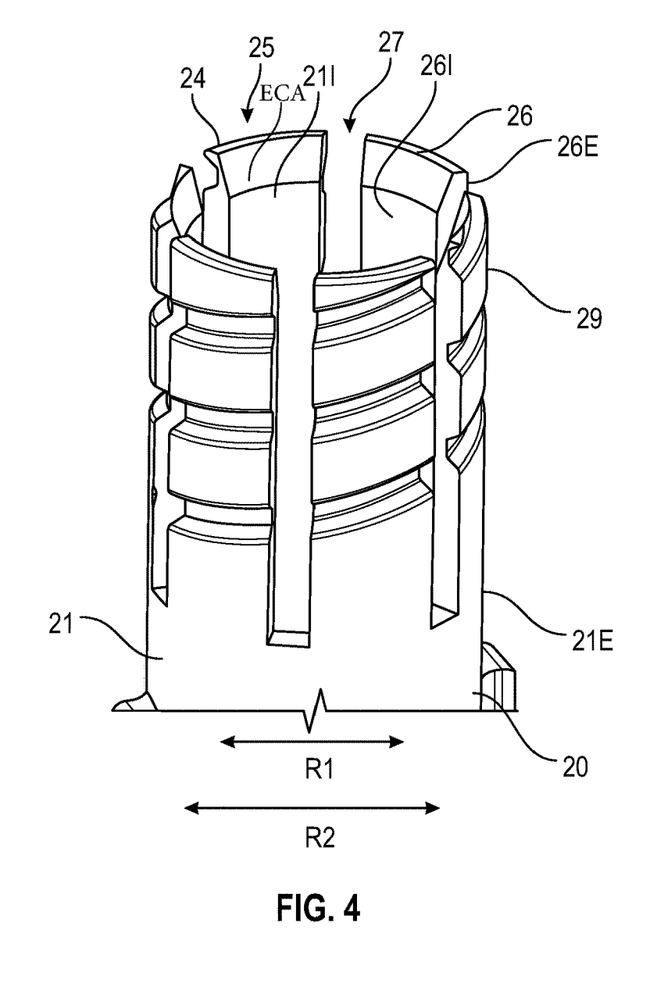
FIG. 4 illustrates a perspective side view of an exemplary split thread protrusion and chamfered entry of the housing shown in FIGS. 1 and 2.

As shown in FIG. 2, housing 20 is a rigid cap having an expandable slitted opening having with slits or cutouts on its lateral surface for flexibility to allow the opening of housing to expand radially outwards based on the diameter of the engaging connector to accommodate different diameters of connectors (NFCs and IV male luers). The housing 20 comprises an integral body having a sidewall 21, closed end 22 having a distal wall 23, and an open end 24. The sidewall 21, closed end 22, distal wall 23, and the open end 24 defining a first chamber 25. In one or more embodiments, the sidewall 21 of housing 20 is essentially cylindrical. The sidewall 21 of housing 20 of the sidewall having an inner surface 21I and an exterior wall surface 21E. The sidewall of the housing having a length LC extending from the closed end 22 to an open end 24 and defining a first chamber 25. A portion of the sidewall 21 of the housing 20 having a length LT extending from the open end 24 toward the closed end 22 includes a split-thread protrusion 26 integrally formed with the sidewall 21 extending from the distal wall 23. A portion of the sidewall of the housing having a length LT includes a split-thread integrally formed with the distal wall. The inner surface of the split-thread protrusion of the sidewall having the flexible container disposed within the first cavity. The open end 24 formed by the cylindrical sidewall 21 having an opening to the first chamber 25 for receiving a flexible container 30 within the housing 20. In one or more embodiments, as shown in FIG. 4, the split-thread protrusion 26 are configured as one or more cantilevered prongs separated by one or more respective gaps or cutouts 27. In an exemplary implementation, at least a portion of one or more of the two or more cantilevered prongs of split-thread protrusion 26 may bend in order to allow better interference fit compliance with the fitting such as at least one of male connector or female connector. In one or more embodiments, at least one of the cantilevered prongs of split-thread protrusion 26 can be configured to bend to facilitate interference fit between the housing 20 and the mating feature of the female needleless connector. The split-thread protrusion 26 of the sidewall having an inner surface 26I and an exterior wall surface 26E. The exterior wall surface 26E of the split-thread protrusion 26 of the sidewall of the housing having one or more threads 29 that are sized and adapted to interlock with a mating feature of the male luer connector. As shown in FIGS. 1 and 4, outer threads 29 of the split-thread protrusion 26 of sidewall of housing 20 extends in a helical pattern. In one or more embodiments, full length or partial length of the prongs on exterior wall surface 26E may be threaded to control how deep the connectors can be threaded into the cavity. This may also facilitate the volume of compression on disinfectant impregnated sponges to control the disinfectant volume that's dispensed upon engagement to connectors.

In an exemplary implementation of FIGS. 3 and 4, housing is illustrated as comprising a plurality of prongs spaced by cutouts 27 and extending essentially from the closed end 22 of housing 20. Referring to FIGS. 1 and 2, in one or more embodiments, the exterior wall surface 21E comprises a plurality of grip members 28.

In one or more embodiments, the flexible container 30 extends essentially parallel to the cylindrical sidewall 21 of the housing 20. In one or more embodiments, flexible container 30 can extend essentially from the distal wall 23 toward the open end 24 of the housing 20.

Figure 5:
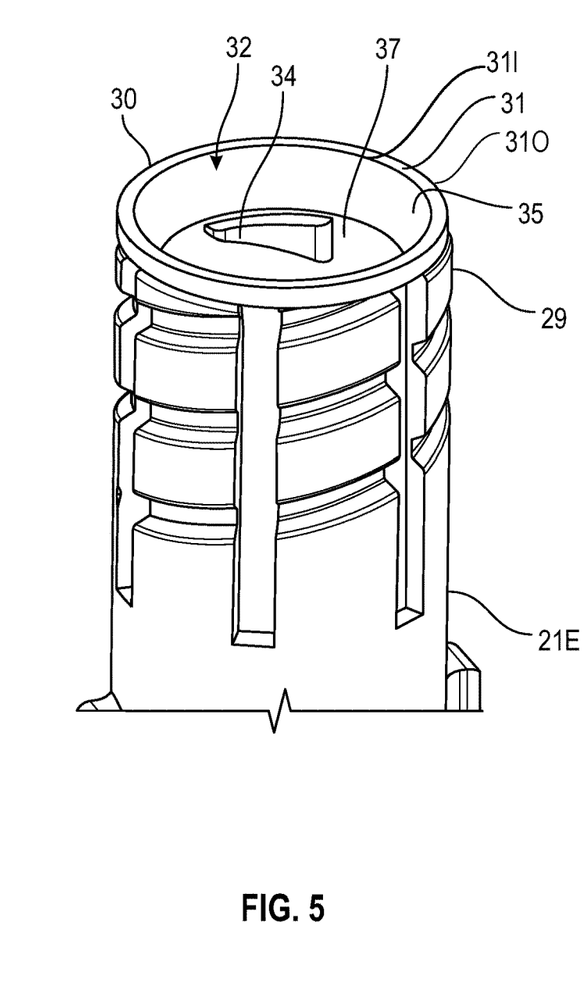
FIG. 5 illustrates a perspective side view of an exemplary split thread protrusion of the housing and a flexible container having an chamfered entry and lug in the inner surface of the flexible container shown in FIGS. 1 and 2.

As shown in FIGS. 2 and 5, the flexible container 30 includes a sidewall 31 defining an inner surface 31I and an outer surface 31O, the inner surface 31I of flexible container 30 defining a second cavity 32. The inner surface 31I of flexible container 30 has a pair of lugs 34 on diametrically opposite sides that has a size and pitch configured to engage a threadable segment of a female connector, such as for example, a female luer connector. In some embodiments, cap 10 provides a protective cover for a female luer connector when engaged with the connector. Specifically, the cap 10 provides a protective cover when threads from the female luer connector engage and form a releasable connection with the lug 34 of flexible container 30. In one or more embodiments, the lug 34 is included on the inner surface 31I of flexible container 30, the lug 34 being sufficient to interlock with a mating feature of the female needleless connector.

Referring to FIG. 1, the flexible container 30 is disposed within first chamber 25 of the housing 20. The flexible container 30 can be essentially cylindrical and coaxial with sidewall 21 of the housing 20. The flexible container 30 has a closed bottom end made of an elastomeric material which can expand along with housing 20. This is bonded to the housing with the lip towards the distal end and near the opening of the housing 20. The elastomeric flexible container creates a better seal on the connectors compared to similar containers currently known in the prior art. The flexible container 30 is disposed within the first chamber 25 of the housing includes an inner surface 31I defining an inner portion of second cavity 32, and an outer surface 33 defined by the outer sidewall of the flexible container 30. In one or more embodiments, the closed end 37 of the flexible container 30 is abutted against the distal wall 23 of the housing 20 when the flexible container 30 is disposed in the first chamber 25 of the housing 20. Flexible container 30 comprises an inner thread or lug 34 disposed on the inner surface 31I for engaging a male connector.

The open end of the flexible container has an entry chamfer 35 on the flexible container 30 that supports entry of the female connector to enable ease in engagement.

A porous absorbent material 40 is assembled into the flexible container 30. In one or more embodiments, the porous absorbent material is a soft sponge. The porous absorbent material 40 retains disinfectant (e.g. isopropyl alcohol (IPA)) in its structure and releases the disinfectant when compressed with an engaging connector. Referring to FIG. 3, in one or more embodiments, a porous absorbent material 40 is disposed within the second cavity 32 of the flexible container. In one or more embodiments, the porous absorbent material 40 is under radial compression by the inner surface 31I of the wall of flexible container 30 to retain the porous absorbent material 40 within the second cavity 32 of the flexible container. In one or more embodiments, the porous absorbent material 40 is a nonwoven material, foam, or a sponge. In a specific embodiment, the foam is a polyurethane foam.

The porous absorbent material 40 comprises an integral body 41, an annular wall 42, a bottom surface 43 and a distal face 44. In one or more embodiments, the foam of the porous absorbent material 40 is saturated or soaked with a disinfectant or an antimicrobial agent. In one or more embodiments, the porous absorbent material 40 is a nonwoven material, foam, or a sponge. In a specific embodiment, the porous absorbent material 40 is polyethylene foam. The foam may be open celled, semi-opened or closed celled. In one or more embodiments, the porous absorbent material 40 is molded, extruded or die cut from sheeting to form a cylindrical block shape. The cap of the present disclosure includes a slitted housing with flexible container with the composite sponge. The absorbent material may include a composite foam with seal rubber at the top and soft sponge underneath to minimize IPA Ingress and retain the disinfectant, respectively.

The cap of the present disclosure provides long-lasting disinfection and prevents microbial entry (has a physical barrier, and ability to retain antimicrobial reagent/'leak proof' connection).

In one or more embodiments, the porous absorbent material 40 also comprises of a centrally disposed opening 45 that is positioned concentrically relative to the annular wall 42 and completely extends from the bottom surface 43 to the distal face 44 of the porous absorbent material 40. In one or more embodiments, as shown in FIGS. 5 through 8, sealing rubber 50 is disposed onto porous absorbent material 40. As shown in FIG. 1, the sealing rubber 50 comprises of an integral body 56, an annular wall 52, a bonded surface 58 and a sealing surface 59. In one or more embodiments, the annular wall 52 of the sealing rubber 50 is disposed into the opening 45 of the porous absorbent material 40. In one or more embodiments, the sealing rubber is stacked on top of the absorbent reservoir material using adhesive. In one or more embodiments, the sealing rubber is bonded to the absorbent material with a biocompatible adhesive.

The sealing rubber 50 is a non-porous sponge bonded to the porous absorbent material 40. The sealing rubber 50 seals the lumen of a male IV luers once engagement with the universal cap begins to prevent or minimize disinfectant (e.g. IPA) ingress into the fluid path of the connector. The possibility of IPA ingress is lower with the use of cap specifically in male luer connectors when compared to ingress in currently available disinfecting caps due to presence of a sealing rubber 50 which seals the lumen of a male IV luers upon engagement. In a specific embodiment, the sealing rubber 50 is in the form of a plug disposed in the center of the porous absorbent material 40. The cap 10 of the present disclosure mitigates ingress of antimicrobial reagent specifically in Male Luer Connectors. The cap of the present disclosure mitigates particulate hazard which occurs when material with tendency to disintegrate can potentially enter the fluid path which constitutes a potential hazard to a patient.

In a specific embodiment, the sealing rubber 50 is closed cell foam. In one or more embodiments, the sealing rubber 50 may comprise of closed cell foams such as PE foams or thermoplastic elastomers (TPE) foams. In one or more embodiment, the sealing rubber 50 may also comprise of rubber or rubber-like foams including: (ethylene propylene diene monomer) EPDM sponges, ethylene-vinyl acetate (EVA), Buna-N, polyethylene sponges, silicone, vinyl, neoprene, fluoroelastomers, gum rubber, or TPE materials. In one or more embodiments, the sealing rubber 50 is molded, extruded or die cut from sheeting to form a cylindrical block shape.

The bonded surface 58 of the sealing rubber 50 is secured to the bottom surface 43 of the porous absorbent material 40. When secured, the annular wall 52 of both the sealing rubber 50 and the porous absorbent material 40 are concentric and coincident. The methods of which the bonded surface 58 and the bottom surface 43 of the porous absorbent material 40 are secured include using adhesives and other appropriate bonding methods. The coincident annular wall 52 of the sealing rubber 50 and the annular wall 42 of the porous absorbent material 40 is appropriately sized to fit into the second cavity 32 of the flexible container 30 having a sdefined by inner surface 31. When assembled, the sealing rubber and the reservoir foam completely fill the inner surface 311 of flexible container 30 defining a second cavity 32. The assembly of the porous absorbent material 40 and the sealing rubber 50 are frictionally fitted into the second cavity 32 formed by the inner surface 311 of flexible container 30.

As the lug 34 of the flexible container 30 is threadably secured to a female luer connector, the luer connector compresses the sealing surface 59 of the sealing rubber 50 towards the closed end 37 of the flexible container 30. Compression of the sealing rubber 50 causes the bonded surface 58 of the sealing rubber 50 to compress the porous absorbent material 40 further into the closed end 37 of the flexible container 30. As a needless connector is threadably secured to the inner threads or lug 34 or outer threads 29, the sealing rubber 50 applies pressure to the lumen of a luer connector. The pressure applied to the lumen of the connector by the sealing rubber 50 blocks the lumen and mitigates the potential of disinfectant ingress into the luer connectors. In one or more embodiments, the sealing rubber 50 is elastic. The pressure applied by the sealing rubber 50 to the connector can range from less than one psi and up to tens of psi. Additionally, the pressure applied by the sealing rubber 50 to the lumen of the luer connector sustains the fluid pressure in the lines of the luer connector to prevent fluid leakage and also prevents ingress of disinfectant into the lumen of the connector.

The cap may further comprise a disinfectant or the antimicrobial agent 70. The cap 10 can achieve disinfection when used on luer connectors by integrating disinfectant or antimicrobial agent in the second cavity 32 of flexible container 30. The disinfectant or antimicrobial agent can be directly included in the second cavity 32 of flexible container 30 such that the disinfectant or antimicrobial agent can be absorbed into sponges or foam material that fills the second cavity 32 of flexible container 30, specifically the porous absorbent material 40. Cap 10 is designed to be compatible in interacting with various disinfectants. In one or more embodiments, the disinfectant or antimicrobial agent may include variations of alcohol or chlorhexidine. In one or more embodiments, the disinfectant or antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorhexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In a preferred embodiment, the disinfectant or antimicrobial agent comprises isopropyl alcohol (IPA). In one or more embodiments, the disinfectant or antimicrobial agent is a fluid or a gel. In a preferred implementation, porous absorbent material 40 is a sponge soaked with isopropyl alcohol (IPA).

Compression of the porous absorbent material 40 and sealing rubber 50 toward the distal wall 23 of housing 20 upon connection to the female luer connector or the male luer connector allows the connector to contact the disinfectant or antimicrobial agent to disinfect the female luer connector or the male luer connector. Compression of the porous absorbent material 40 causes the antimicrobial or disinfectant to be excreted from the porous absorbent material 40, thereby disinfecting the female luer connector or the male luer connector. The cap 10 of the present disclosure maximizes disinfecting area (e.g., threads, luer top surface, lumen external surface) and minimizes the entry of antimicrobial reagent to enter fluid path.

In one or more embodiments, as shown in FIG. 3, the cap includes a cover 60.

Cover 60 seals the internal contents of the cap 10 after assembly and maintains the sterility of the device. The cover 60 minimizes entry of potential particulate hazard and also provides a substantially impermeable enclosure for the cap 10. In one or more embodiments, the cover 60 may be disposed on and sealed with the lip of flexible container 30. Referring to FIG. 2, in one or more embodiments, the cover 60 is disposed on the concentric non-slitted sidewall of housing 20 via friction fit to prevent the disinfectant or the antimicrobial agent from exiting the second cavity 32. The cover 60 further ensures sterility of the housing 20. The cover 60 provides a leak prevention and protection enclosure, protects the contents of porous absorbent material 40 contained within the first chamber 25, and/or maintains a sealed, sterilized environment. The cover 60 provides a sufficient seal at a range of temperatures, pressures, and humidity levels.

In one or more embodiments, as shown in FIG. 1, the cap may also include a peel seal 80. The peel seal reduces spillage or evaporation of the disinfectant. In one or more exemplary implementation, in addition to cover, a peel seal 80 can also be provided to a surface of a rim of the open end of the flexible container 30 to seal the opening prior to use of cap 10. In one or more embodiments, the peel seal comprises an aluminum or multi-layer polymer film. In one or more embodiments, the peel seal further comprises a moisture barrier. Referring to back to FIG. 1, rim of an open end of flexible container 30 defines an engagement surface where a cover 60 or peel seal 80 may be secured. Peel seal 80 may be attached to the flexible container 30 by heat seal.

In one or more embodiments, the peel seal 80 as shown in FIG. 1 comprises an aluminum or multi-layer polymer film peel back top. In a specific embodiment, the peel seal 80 is heat-sealed or induction sealed to the open end of the flexible container 30. In one or more embodiments, the cover 60 and or peel seal 80 comprise a moisture barrier.

Referring to FIGS. 1 through 9, according to exemplary embodiments of the disclosure, cap 10 can receive a tip or hub of a male connector 92 or female needleless connector 90, for example after the cover 60 is removed or when peel seal 80 sealing second cavity 32 of the flexible container is pierced or removed, within second cavity 32 and secure, for example, threadedly via lug 34 or outer thread 29 as described above. One or more lugs or threads can be sufficient to interlock with a hub or tip of needleless connector.

The cap 10 is made from any of several types of plastic materials such as polycarbonate, polypropylene, polyethylene, polyethylene terephthalate, polylactide, acrylonitrile butadiene styrene or any other moldable plastic material used in medical devices. In one or more embodiments, the cap 10 comprises a polypropylene or polyethylene material. In one or more embodiments, the cover or cap may be made of a high density polyethylene (HDPE) or polypropylene (PP) material.

As shown in FIGS. 1 and 4, the housing 20 comprises a proximal portion having a uniform non-slitted cylindrical sidewall and a distal portion having a slitted sidewall, the distal portion is bounded by a rim and end face located at an open proximal end 24 of the housing. The first chamber 25 within the housing 20 is configured for receiving a flexible container 30 and the second cavity 32 of the flexible container 30 is configured for receiving a needleless connector or a male needleless connector. Opposite to the open end of the first chamber 25 is a distal wall 23.

In one or more embodiments, an outer thread 29 can be included on the exterior wall surface 21E of the split-thread sidewall of the housing 20, the outer thread 29 being sufficient to interlock with a mating feature of the male connector.

As shown in FIG. 4, the sidewall of the split-thread at the distal end of the housing tapers outwardly to create an entry chamfer angle (ECA) and extends to a radius R2 which is larger than the radius R1 of the split-thread housing. The radius R2 corresponds substantially to the largest radius of the split-thread housing.

In one or more embodiments, prior to connection with a connector, the minimum diameter of the NFC thread is 6.73 mm, the Lug diameter is 4.9 mm and the amount of expansion is about ~1 mm radially. In one or more embodiments, the maximum diameter of a needle-free connector thread is 7.6 mm and the maximum diameter of the Universal Disinfecting Cap (UDC)=5.9 mm and the amount of expansion is ~0.75 mm radially.

As shown in FIG. 5, inner threads or lug 34 on the inner sidewall of the flexible container 30 may be tapered and may extends in a helical pattern.

In one or more embodiments, the flexible container 30 and the housing 20 can be bonded together with solvent resistant biocompatible adhesive.

The porous absorbent material 40 surrounds the sealing rubber 50. The nonporous sealing rubber 50 and the porous absorbent material 40 are positioned within the inner surface 311 of flexible container 30 defining a second cavity 32 where the sealing surface 59 will be in contact with the lumen of open luer connectors. In one or more embodiments, the sealing rubber is stacked on top of the absorbent reservoir material using adhesive. In one or more embodiments, the sealing rubber is bonded to the absorbent material with a biocompatible adhesive.

In some embodiments, the connector comprises a needleless injection site, which may sometimes be referred to as a needleless injection port, hub, valve, or device, or as a needleless access site, port, hub, valve, or device. In some embodiments, the cap can be connected with any of a variety of different needleless injection sites. In one or more embodiments, after the cap has been coupled with connector, it is unnecessary to disinfect (e.g. treat with an alcohol swab) the connector prior to each reconnection of the connector with another connector, as the connector will be kept in an uncontaminated state while coupled with the cap. Use of the cap replaces the standard swabbing protocol for cleaning connectors.

Another aspect of the present disclosure pertains to a method of disinfecting a medical connector. The method comprises connecting the cap of one or more embodiments to a medical connector, wherein connecting includes engaging the threads of the medical connector onto the threads on the inner or outer surface of the flexible container of the present disclosure upon insertion of the medical connector into the cap such that the medical connector contacts the absorbent material and the disinfectant or antimicrobial agent.

Figure 6:
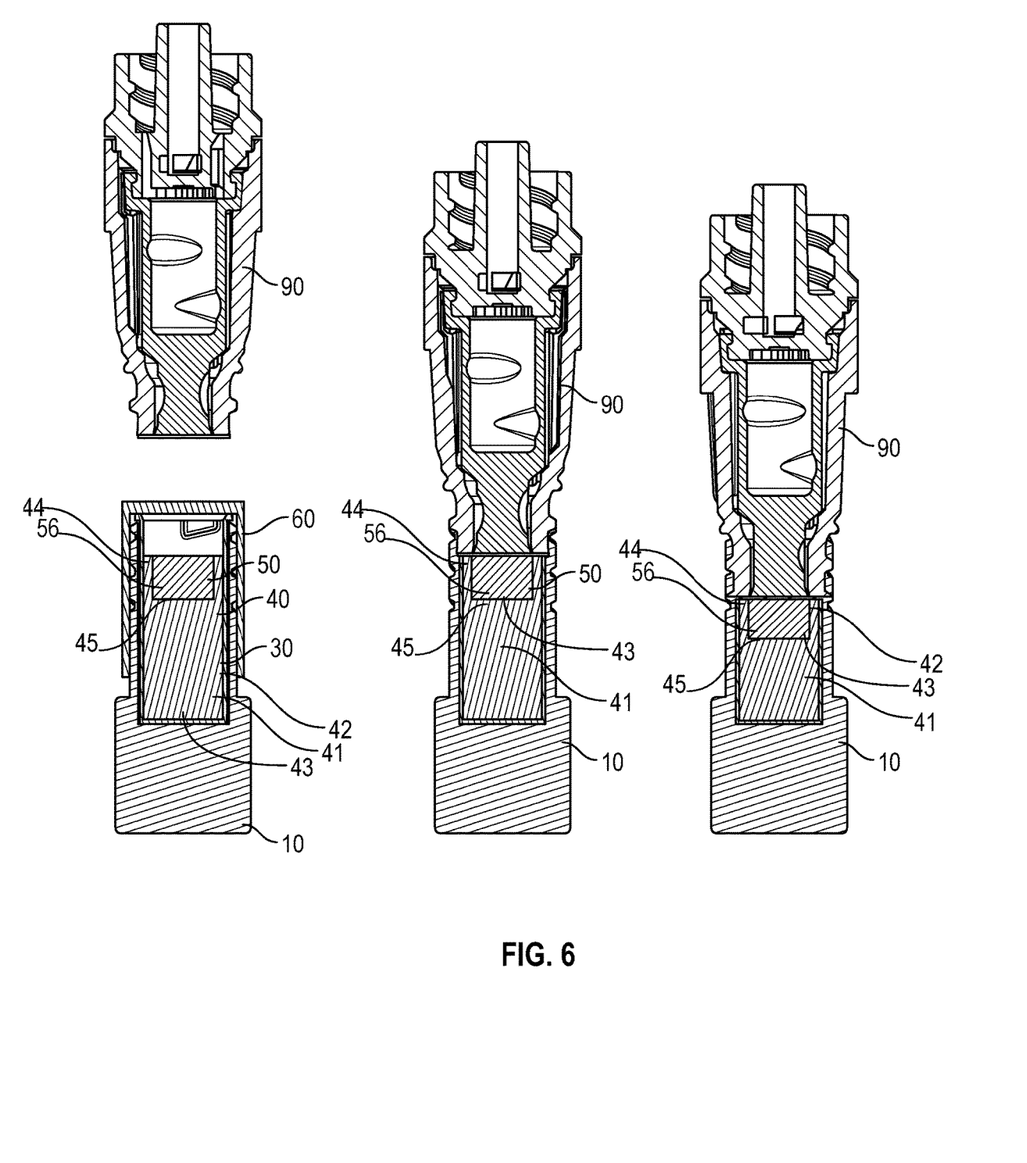
FIG. 6 illustrates a cross-sectional view of an exemplary assembled cap with a female connector.
Figure 7:
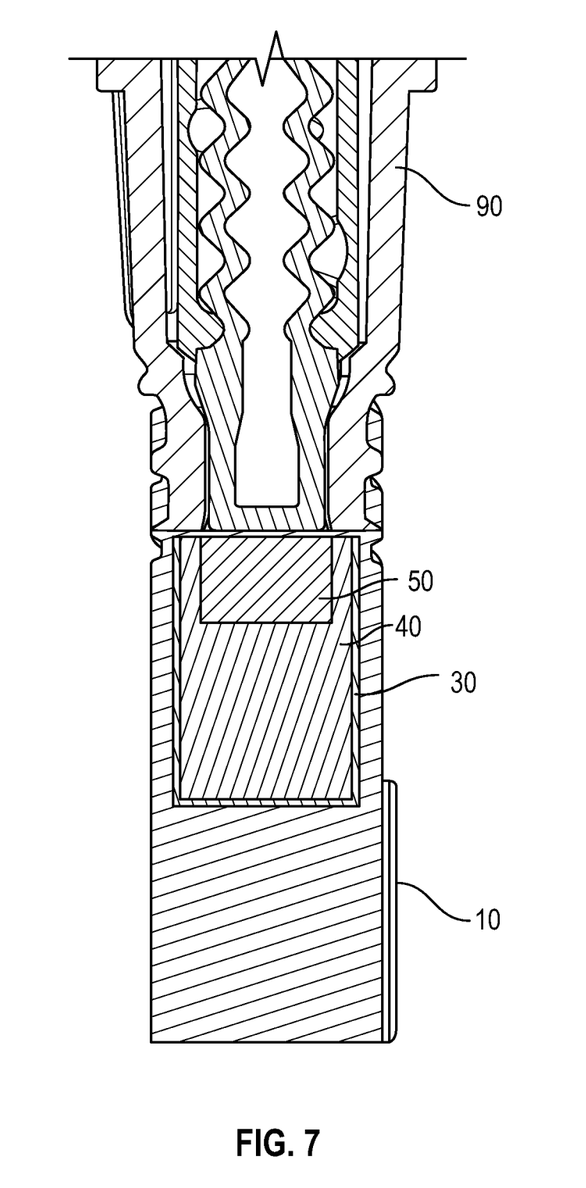
FIG. 7 illustrates a cross-sectional view of an exemplary assembled cap in connection with a female connector of various types superimposed on each other, as shown in FIG. 6.

FIGS. 6 and 7 illustrates a cross-sectional view of an exemplary assembled cap with a female connector 90. FIG. 7 illustrates a cross-sectional view of an exemplary assembled cap in connection with a female connector of various types superimposed on each other, as shown in FIG. 6. To connect the cap of the present disclosure with a female connector or needle free connector (NFC), the user removes cover on the cap and engages the outer thread of the female connector or needle free connector (NFC) which interacts with the Entry chamfer on the flexible container 30. Axial movement of the female connector into the Cap flares out the housing and opens space for the NFC. To accommodate the engaging needle free connector (NFC), the slits in the housing expand. Since the flexible container is also bonded to the housing, the flexible container also expands radially outwards. Due to this expansion, the female luer connector or needle free connector (NFC) enters deeper into the cap and encounters a pair of diametrically opposite lugs (portion of threads). NFC threads initially overrides the lugs and then engages with lugs for further movement. Lugs present on the inner surface then engage with the threads of the female luer connector or needle free connector (NFC) and a secure connection is established. The lugs are disposed slightly away from the entry point which enables easy entry into the cap. Due to axial movement of female luer connector or needle free connector (NFC) into the cap, sealing rubber and in turn absorbent material get compressed and disinfectant or antimicrobial agent is released which wets and disinfects the septum and threads of female luer connector or needle free connector (NFC). The sealing rubber, which is wetted with disinfectant, contacts the septum of female luer connector or needle free connector (NFC). The sealing rubber seals the face of female luer connector or needle free connector (NFC) and forms a physical barrier to prevent ingress disinfectant or antimicrobial agent into the lumen of the luer.

Figure 8:
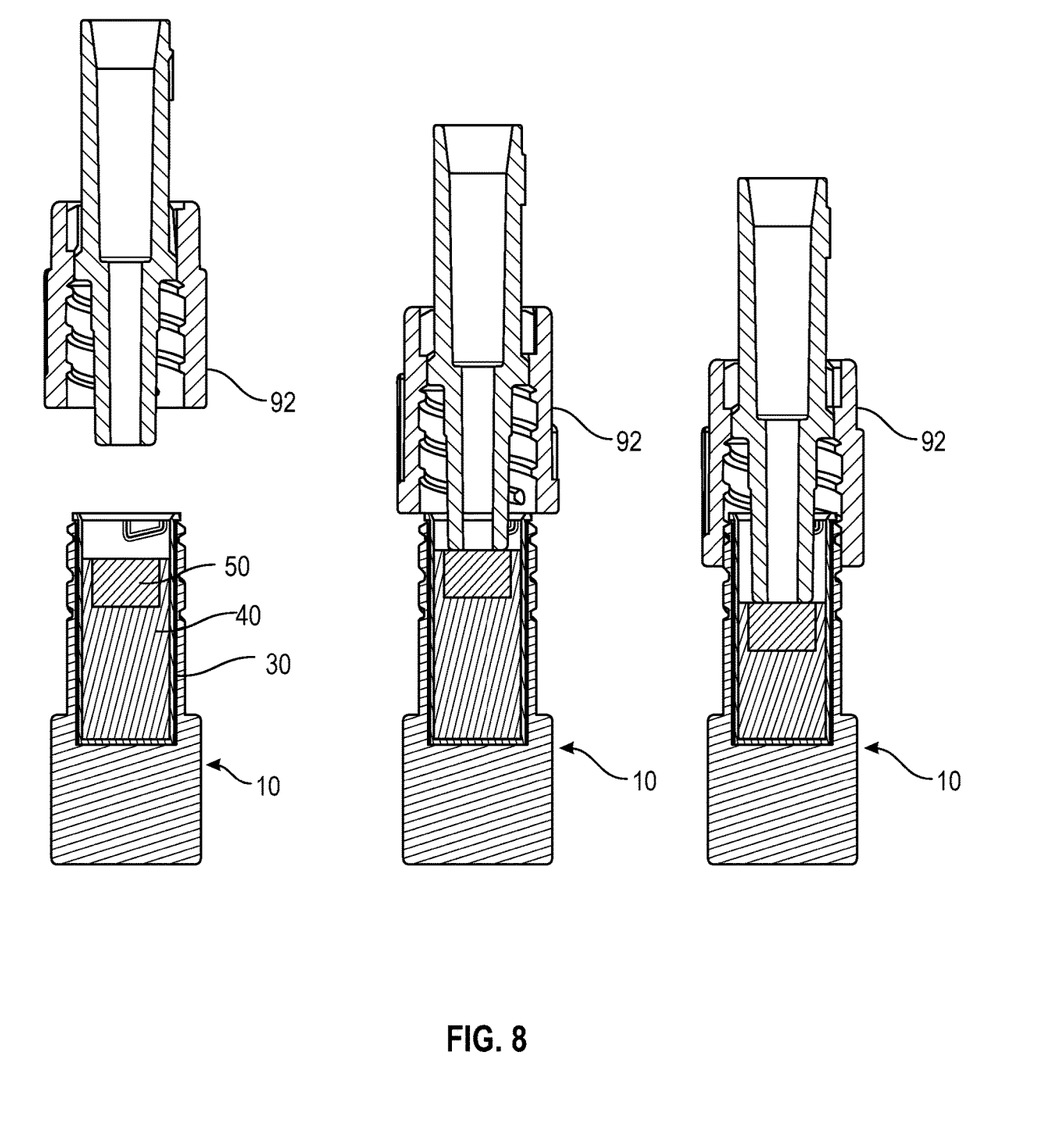
FIG. 8 illustrates a cross-sectional view of an exemplary assembled cap with a male connector.
Figure 9:
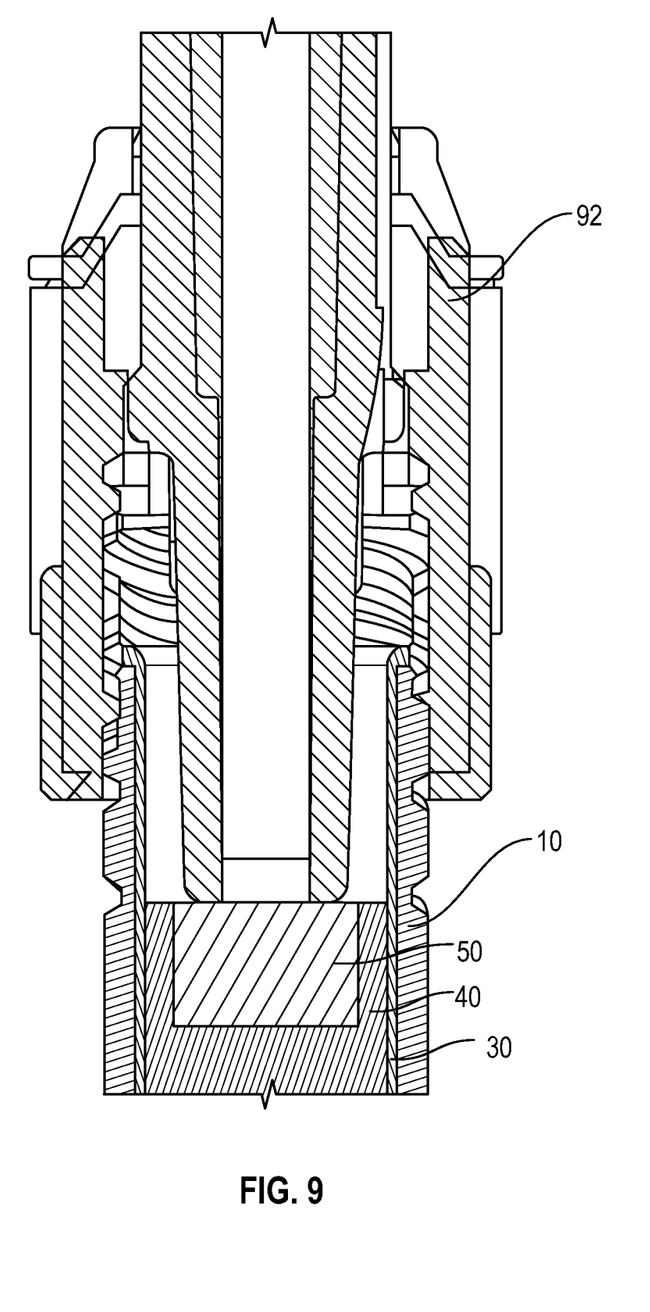
FIG. 9 illustrates a cross-sectional view of an exemplary assembled cap in connection with a male connector of various types superimposed on each other, as shown in FIG. 8.

FIGS. 8 and 9 illustrates a cross-sectional view of an exemplary assembled cap with a male connector 92. FIG. 9 illustrates a cross-sectional view of an exemplary assembled cap in connection with a male connector of various types superimposed on each other, as shown in FIG. 8. To connect the cap 10 of the present disclosure with a male connector, such as a male luer on an IV line, the user removes the cover 60 on the cap 10 and engages the threads in the connector with the inner threads or lug 34 or outer threads 29 on the housing 20. Outer collar of the connector engages with the threads present on the housing. Outer threads 29 engage with the inner threads of the male collar. The housing 20 is extracted from the male connector collar. The part connects nominally with the male connector. No expansion or compression of the slitted opening of the housing takes place since the threads are complementary to each other. When the male luer enters into the cap 10, the face of male luer lumen first contacts the sealing rubber 50 wetted with disinfectant, which upon further compression creates a seal at the interface. The sealing rubber 50 seals the face of male luer and forms a physical barrier and stops disinfectant or antimicrobial agent ingress into the fluid path. This does not allow disinfectant or antimicrobial agent in the cap to ingress into the lumen of the luer. The absorbent material gets compressed during engagement and disinfectant or antimicrobial agent stored in its structure is released. This disinfects the luer outer surface of the male connector.

The universal cap of the present disclosure allows for disinfection of all clinically relevant areas including threads, luer top surface, and the lumen external surface.

The exemplary caps of the present disclosure are capable of capable of blocking the lumens of open luers to minimize ingress of disinfectant and microbial agents into connectors for both female luer connector and male luer connector, thereby reducing risk of the disinfectant and microbial agents entering the blood stream of a patient.

While the present disclosure has been shown and described with reference to certain exemplary embodiments thereof, it will be understood by those skilled in the art that various changes in form and details may be made therein without departing from the spirit and scope of the embodiments of the present disclosure. For example, a absorbent material can comprise any suitable disinfecting or other application-specific substance, and can be made of any suitable material. Also, the housing of the cap can be single shot molded, or made by other suitable process. Furthermore, any of the features or elements of any exemplary implementations of the embodiments of the present disclosure as described above and illustrated in the drawing figures can be implemented individually or in any combination(s) as would be readily appreciated by skilled artisans without departing from the spirit and scope of the embodiments of the present disclosure.

In addition, the included drawing figures further describe non-limiting examples of implementations of certain exemplary embodiments of the present disclosure and aid in the description of technology associated therewith. Any specific or relative dimensions or measurements provided in the drawings other as noted above are exemplary and not intended to limit the scope or content of the inventive design or methodology as understood by artisans skilled in the relevant field of invention.

Other objects, advantages and salient features of the disclosure will become apparent to those skilled in the art from the details provided, which, taken in conjunction with the annexed drawing figures, disclose exemplary embodiments of the disclosure.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A cap comprising:
a housing having closed distal end comprising a distal wall, an open proximal end, a cylindrical sidewall extending proximally from the distal wall toward the open proximal end, a cylindrical sidewall forming a first cavity, the cylindrical sidewall having a split-thread protrusion integrally formed with the distal wall, the split-thread protrusion having an inner surface and an outer surface, the inner surface of the split-thread protrusion defining a first cavity,
a flexible container disposed in the housing and positioned within the first cavity, the flexible container having a closed distal end comprising a distal wall, an open proximal end, a sidewall extending proximally from the distal wall toward the open proximal end, the sidewall integrally formed with the distal wall, the sidewall having an inner surface and an outer surface, the inner surface of the flexible container defining a second cavity,
an outer thread on the outer surface of the split-thread protrusion of the housing, the outer thread being sufficient to interlock with a mating feature of a male connector;
an open bottom formed by the cylindrical sidewall with an opening to the first cavity within the housing for receiving a needleless connector having an open lumen;
an inner thread or a lug on the inner surface of the flexible container, the inner thread being sufficient to interlock with a mating feature of a female needleless connector,
a porous absorbent material disposed within the second cavity under radial compression by the inner thread on the inner surface of the flexible container; and
a sealing rubber is disposed on the porous absorbent material;
a disinfectant or an antimicrobial agent; and
a cover disposed over the proximal open end of the housing.

2. The cap of claim 1, wherein the porous absorbent material is a nonwoven material, foam, or a sponge.

3. The cap of claim 1, wherein the porous absorbent material is soaked with a disinfectant or an antimicrobial agent.

4. The cap of claim 1, wherein the sealing rubber is made of a closed cell foam.

5. The cap of claim 4, wherein the sealing rubber is made of a polyethylene foam.

6. The cap of claim 4, wherein the sealing rubber is made of a thermoplastic elastomer.

7. The cap of claim 4, wherein the sealing rubber is made of a rubber or rubber like foams.

8. The cap of claim 7, wherein the sealing rubber is an EPDM sponges, EVA, Buna-N, silicone, vinyl, neoprene, fluoroelastomers, gum rubber.

9. The cap of claim 1, wherein the flexible container extends essentially from an inner surface of the distal wall toward the open proximal end of the housing.

10. The cap of claim 1, wherein the flexible container extends essentially parallel to the sidewall of the housing.

11. The cap of claim 1, wherein the inner thread and the outer thread have an inclined thread pattern.

12. The cap of claim 1, wherein the inner thread and outer thread have a helical-shaped thread pattern.

13. The cap of claim 1, wherein an exterior wall surface of the sidewall of the housing includes a plurality of grip members.

14. The cap of claim 1, further comprising a disinfectant or an antimicrobial agent.

15. The cap of claim 14, wherein the disinfectant or the antimicrobial agent is selected from isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, or mixtures thereof.

16. The cap of claim 1, wherein the housing is made of a high density polyethylene or polypropylene material.

17. The cap of claim 1, further comprising a peel seal.

18. The cap of claim 17, wherein the peel seal includes an aluminum or multi-layer polymer film.

19. The cap of claim 1, wherein the porous absorbent material comprises a centrally disposed through hole extending from a distal end to a proximal end of the porous absorbent material.

20. The cap of claim 19, wherein the sealing rubber is disposed in the through hole of the porous absorbent material.

21. The cap of claim 20, wherein the porous absorbent material surrounds the sealing rubber.

22. The cap of claim 19, wherein the sealing rubber is bonded to the absorbent material with a biocompatible adhesive.

* * * * *